United States Patent [19]

Hilger et al.

[11] Patent Number: 5,555,180
[45] Date of Patent: Sep. 10, 1996

[54] METHOD FOR PROCESSING DIGITIZED ULTRASONIC SIGNALS ORIGINATING FROM AN ULTRASONIC PROBE FOR THE STORAGE OF AND LATER RECONSTRUCTION OF THE ULTRASONIC SIGNALS FROM THE STORED DATA

[75] Inventors: Heinz-Josef Hilger, Am Kreuz; Manfred Rehrmann, Hurth; Norbert Steinhoff, Erftstadt, all of Germany

[73] Assignee: Krautkramer GmbH & Co., Hurth, Germany

[21] Appl. No.: 219,101

[22] Filed: Mar. 29, 1994

[30] Foreign Application Priority Data

Mar. 29, 1993 [DE] Germany ............................ 43 10 134.8
Oct. 1, 1993 [DE] Germany ............................ 43 33 531.4

[51] Int. Cl.$^6$ .................................................... G06F 7/00
[52] U.S. Cl. ...................... 364/577; 364/715.06; 364/721
[58] Field of Search .......................... 364/715.01, 715.06, 364/721, 577, 723, 608

[56] References Cited

U.S. PATENT DOCUMENTS

| | | | |
|---|---|---|---|
| 4,238,831 | 12/1980 | Pulyer | 364/608 |
| 5,075,880 | 12/1991 | Moses et al. | 364/723 |
| 5,126,960 | 6/1992 | Thong | 364/721 |
| 5,321,642 | 6/1994 | Goldberg | 364/721 |

*Primary Examiner*—James P. Trammell
*Attorney, Agent, or Firm*—Michael J. Kline; Darren E. Wolf; Carol I. Bordas

[57] ABSTRACT

A method for processing digitized ultrasonic signals originating from an ultrasonic probe for the storage and later reconstruction of the ultrasonic signals from the stored data. Each half-wave from the digitized data is stored as the maximum amplitude, polarity sign, and location on the time axis of the wave. Reconstruction of the signal from the stored data is effected by constructing a series of 180° cosine curves from the stored data and connecting each successive cosine curve with the previous cosine curve.

9 Claims, 5 Drawing Sheets

Time

Sample points

METHOD FOR PROCESSING DIGITIZED ULTRASONIC SIGNALS ORIGINATING FROM AN ULTRASONIC PROBE FOR THE STORAGE OF AND LATER RECONSTRUCTION OF THE ULTRASONIC SIGNALS FROM THE STORED DATA

FIELD OF THE INVENTION

The invention relates to a method for processing digitized ultrasonic signals originating from an ultrasonic probe for the storage and later reconstruction of the ultrasonic signals from the stored data.

BACKGROUND OF THE INVENTION AND PRIOR ART

According to the state of the art the high-frequency signals received by the ultrasonic probes are digitized and can then be further processed by digital computers. The high frequency signals are also referred to as ultrasonic signals or as a so-called A-image. In the course of the further processing, a link can be made to the path coordinates of the measuring points, an evaluation and true-to-location representation of the test results (so-called B-, C- or D- images) can be performed, the measured results from several tests carried out in sequence on the same test object can be stored in order to determine changes, an analysis process can be carried out for the purposes of flaw reconstruction using known algorithms.

For most evaluation methods the signal travel time and/or the actual high-frequency signal waveform (the ultrasonic signal) is required in addition to the maximum signal amplitude in each flaw expectation range. For the digital processing the analogue signals must therefore be sampled at a multiple of the probe frequency in order to be able to sample the actual signal waveform with the required accuracy, i.e. in order to achieve the required accuracy for these evaluation methods. The relationship between probe frequency, sampling rate and sampling error is known: the higher the sampling rate selected in relation to the probe frequency, the lower is the sampling error.

If, for example, a probe signal with 15 MHz is to be digitized with a sampling error of 0.1 dB, then the sampling rate must be at 300 MHz. For an evaluation range of e.g. 100 mm (steel, longitudinal) this results for a single test shot in a volume of data of 10,240 digital measured values. If one assumes a testing density of one shot per millimeter of path, then this results in 10,240,000 measured values for a test path of 1 meter.

In practice, however, not only one but several, for example 2 to 16 and more test functions are provided for automatic tests and in addition high test speeds (e.g. 500 mm/s or greater) are necessary. On the basis of these standards up to 81,920,000 measured values per second would result for said example.

These amounts of data cannot be processed in real time with the economically feasible computers in practical use today and also cannot be stored.

In practice digitization is therefore only carried out at 100 MHz, thus a compromise is made between sampling error and the number of measured values arising. In addition the digitized data are reduced to maximum amplitude values per section of the travel path, e.g. 1 value per x mm. A reconstruction of the signal form to the degree of accuracy required for evaluation methods is however no longer possible with these values.

SUMMARY OF THE INVENTION

At this point the invention comes in. It has the object of providing a method for the processing of digitized ultrasonic signals originating from a probe, which requires only a small amount of storage space and which nevertheless enables a later reconstruction of the ultrasonic signals from the stored data.

This object is achieved by the method with the characteristics stated in Patent claim 1.

With this method an ultrasonic signal is digitized with the high digitization rate necessary for the admissible sampling error. For each half-wave from the digitized data only the value of the maximum amplitude, its polarity sign and its location on the time axis are stored. All further digitized values are not considered for storage. It is possible to reconstruct the original ultrasonic signal using only these values because the ultrasonic signals are essentially determined by the probe frequency, and therefore have practically no upper or lower waves.

The reconstruction of the ultrasonic signals, i.e. of the high-frequency signal waveform, from the stored values is now effected in such a way that two neighboring maximum amplitudes, of which one always has a positive sign and the other a negative sign, are connected by a 180° cosine curve, which has a slope of zero at the position of the maximum amplitudes. This makes it possible to reconstruct the original signal form with sufficient accuracy for the later evaluation.

The method has the advantage that on the one hand the high digitization frequency required for the digitization (accuracy) can be used, but only two values per complete oscillation must be processed by the digital computers, with which values the signal reconstruction can also be performed.

With this method the amount of data stated above can be reduced by approximately a factor of ten. Such a reduced amount of data can be processed by the computers in practical use today. In particular however, in contrast to reduction processes for data know to date, the signal form can be reconstructed from the reduced data with an accuracy sufficient for the further processing.

BRIEF DESCRIPTION OF THE DRAWINGS

The method according to the invention is explained and described in the following on the basis of figures. Those figures show in.

DETAILED DESCRIPTION OF THE PREFERRED EMBODIMENTS

Figure 1:
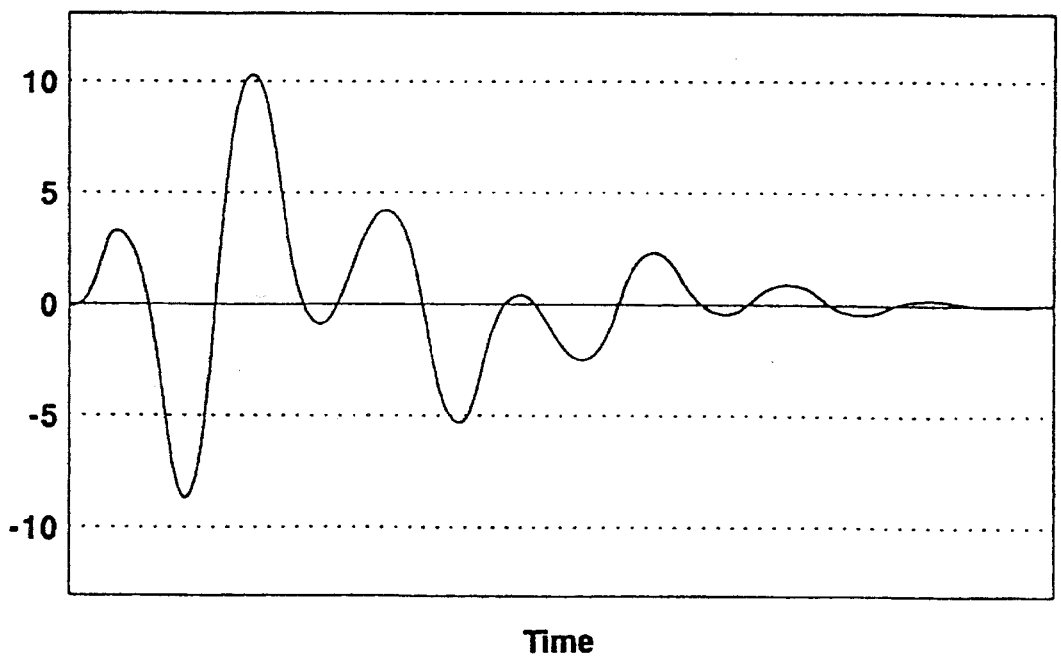
FIG. 1 an ultrasonic signal in high-frequency representation, the amplitude U is plotted against the time t, FIG. 2 the ultrasonic signal from FIG. 1, superimposed in addition on a digitization grid with sufficiently high digitization frequency, FIG. 3 the ultrasonic signal from FIG. 1 in high-frequency representation, shown are the digital amplitude values, FIG. 4 in high-frequency representation only the maximum amplitude values of the representation from FIG. 3 with their correct polarities, FIG. 5 in high frequency representation the reconstruction of the originally analogue probe signal (ultrasonic signal) from the reduced data from FIG. 4, FIG. 6 a representation to explain the reconstruction algorithm, FIG. 7 a block diagram of the circuitry used, and FIG. 8 a representation corresponding to FIG. 5 for a different signal waveform, shown is an evaluation corresponding to FIG. 6.
Figure 2:
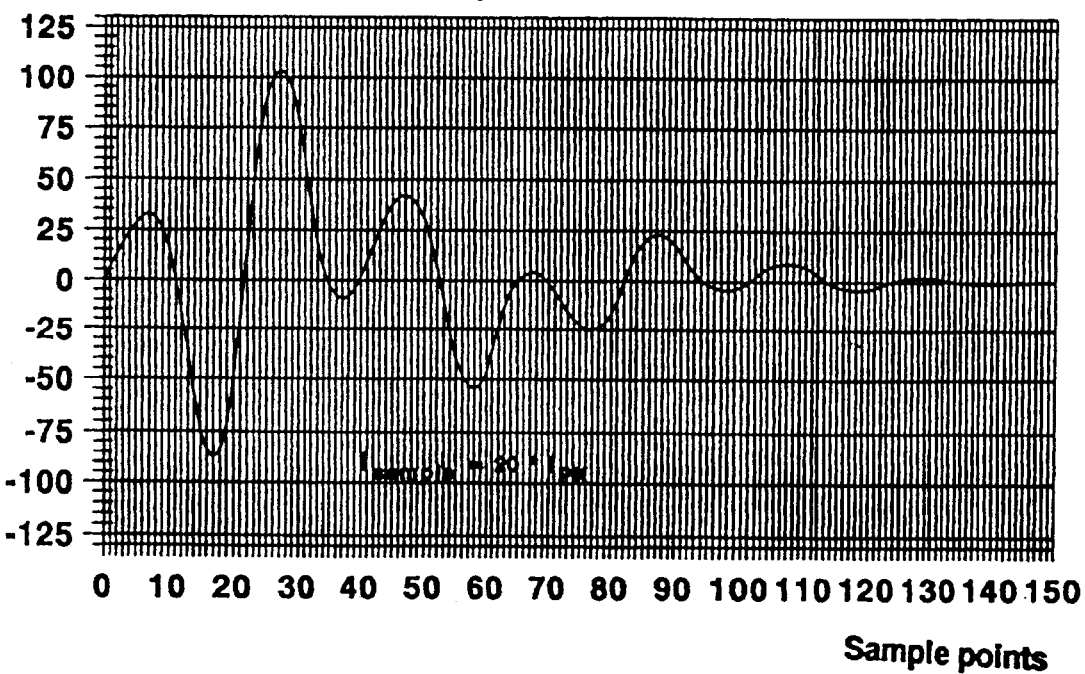

The processing of the analogue probe signal to a reduced representation can be seen step-by-step from FIGS. 1 to 4. The ultrasonic signal according to FIG. 1 is a typical output signal U(t) of a probe. If it is digitized, i.e. superimposed on a digitization grid, as can be seen from FIG. 2, then one receives the representation shown in FIG. 3 of the digital sampling points against the time t, i.e. in high-frequency representation. In other words, the continuous curve path from FIG. 1 is now exploded into a point-by-point curve path as is known from the digital representation. One could also represent FIG. 3 with a multitude of individual bars going from the zero line (time line, x-axis) and extending to the relevant indicated point. But then the representation would be practically no longer comprehensible in a real case.

Figure 3:
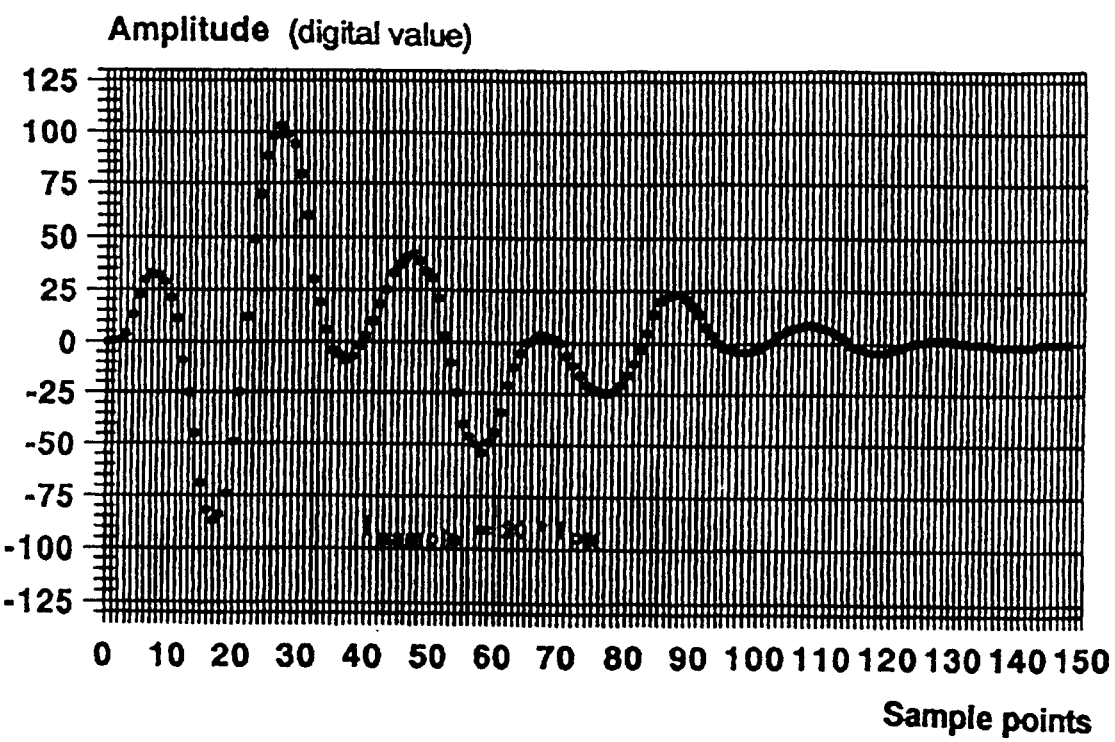
Figure 4:
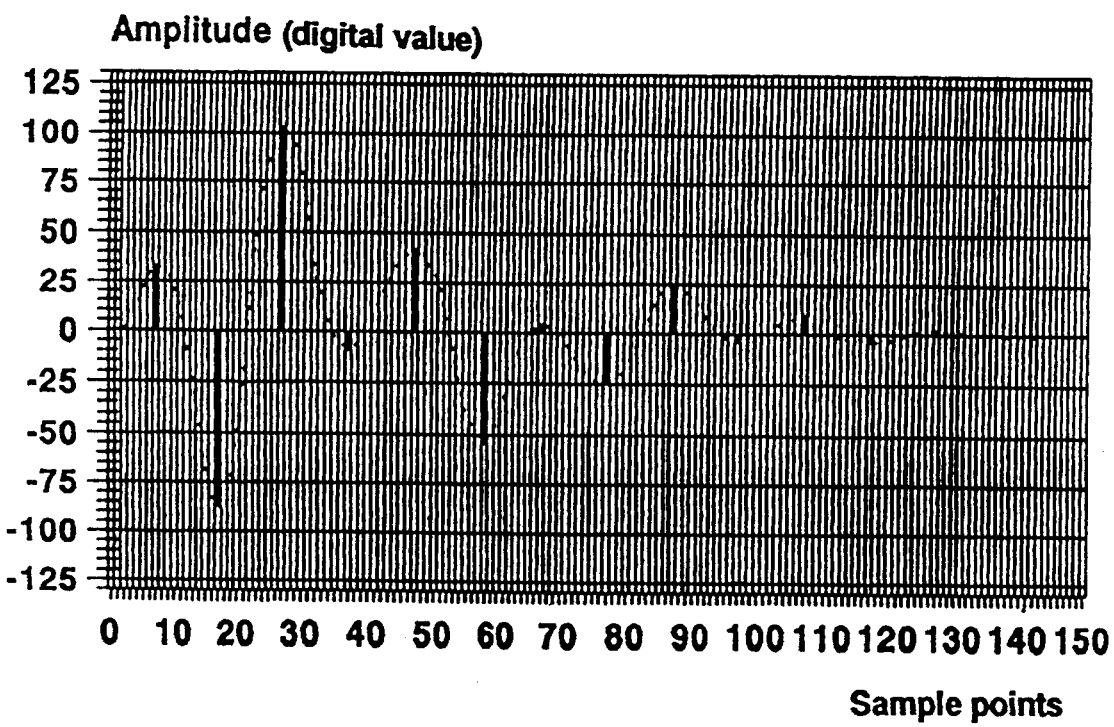
Figure 5:
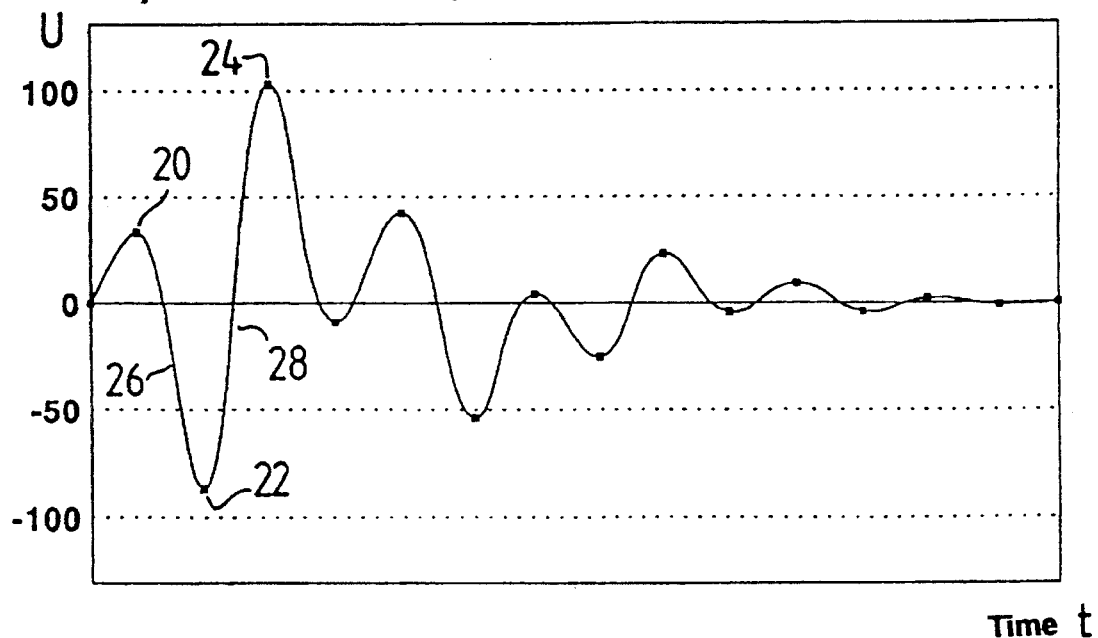

A decisive aspect of the invention is now to be found in the transition from FIG. 4 to FIG. 5. From the multitude of the digital values shown in FIG. 3 only those values continue to be taken into consideration which are the largest values for a half-wave and these are referred to as maximum amplitudes irrespective of their polarity sign. The sign determines whether it is a maximum or minimum value. This simplifies the later description of the reconstruction of the ultrasonic signal from the reduced data.

Following the data reduction, there is therefore one maximum amplitude value, its corresponding time value and the sign of the maximum amplitude value present for each half-wave. A considerable reduction has occurred in comparison with the multitude of the digital values shown in FIG. 3, and this can be immediately seen by comparing FIGS. 3 and 4. In spite of the high data reduction it is possible to reconstruct the original output signal for the most part, as will be shown on the basis of FIG. 5 and the later figures and description.

FIG. 5 once again shows the maximum values corresponding to FIG. 4 in the same time representation as in FIG. 4. The maximum values, also referred to as nodes of interpolation, have the reference numbers 20, 22, 24, etc. It is now possible with an algorithm to connect these nodes of interpolation 20, 22, 24 with one another in such a way that the ultrasonic signal according to FIG. 1 can be reconstructed for the most part.

For the reconstruction two neighboring nodes of interpolation, e.g. 20 and 22, are connected to each other by a 180° cosine curve 26 (a cosine curve from 0° to 180°). This enters with a slope of zero into the two nodes of interpolation 20 and 22 respectively. The same procedure is carried out with the next nodes of interpolation, i.e. 22 and 24. Here once again a 180° cosine curve 28 is used to connect the two nodes of interpolation 22, 24, which in turn arrives with a slope of zero in the nodes of interpolation 22, 24. Due to the inverse sign of the nodes of interpolation 22, 24 the branch 180° to 360° of the cosine curve is used here. In this way the complete curve shape is reconstructed step-by-step, the procedure always being to move forward from the preceding node of interpolation to the adjacent node of interpolation.

Figure 6:
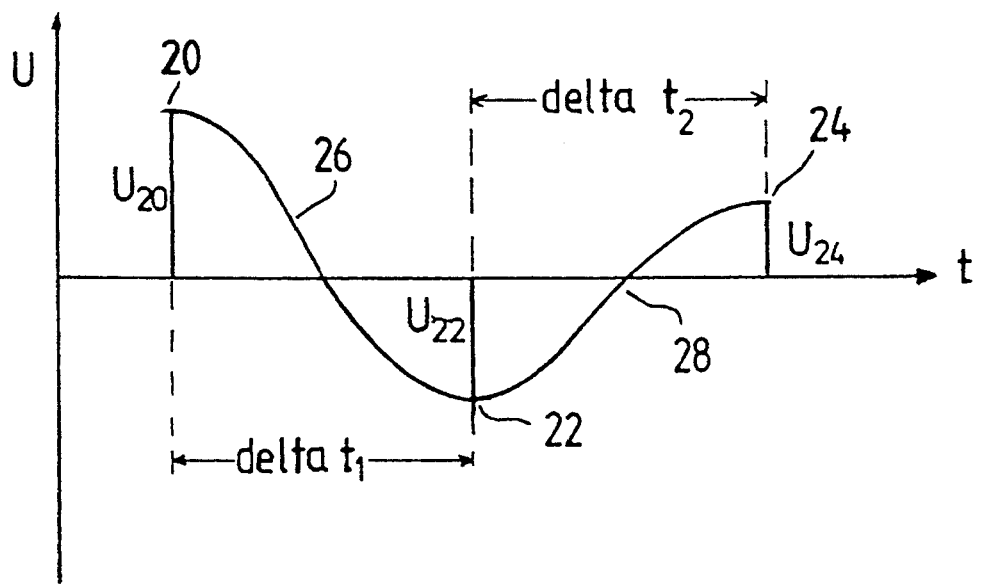

The algorithm described in this way for the reconstruction is again explained in detail on the basis of FIG. 6. Shown in real time are the nodes of interpolation 20, 22, 24, as they can be derived from the reduced representation. $U_{20}$ is the amplitude value of the node of interpolation 20, $U_{22}$ is the amplitude value of the node of interpolation 22, which has a negative sign, $U_{24}$ is the positive amplitude value of the node of interpolation 24. The time interval between the two nodes of interpolation 22 and 20 is delta $t_1$ and the time interval between the next two nodes of interpolation 24 and 22 is delta $t_2$. The reconstruction between the nodes of interpolation 20 and 22 now results from the formula $$U_i = \frac{|U_{20}| + |U_{22}|}{2} \cdot \cos\left[\frac{\text{delta } t_1 \cdot i}{n}\right] + \frac{U_{20} + U_{22}}{2}$$

Here i has the value 0 to n and is incremented, whereby n plus 1 points of a 180° cosine curve result, which extends from the maximum amplitude 20 to the amplitude maximum 22 and enters both maximum amplitudes with a slope of 0°. The computation procedure is as if the zero line did not exist and both nodes of interpolation 20, 22 are treated as if they were located on the maximum amplitude values of a cosine curve.

In the same way the connection is achieved between the nodes of interpolation 22 and 24; because reconstruction is from a negative to a positive amplitude value, however, 180 degrees are added to the argument of the "cos" in the formula.

The connection between the two following nodes of interpolation is then again carried out according to the cosine formula stated above.

Figure 7:
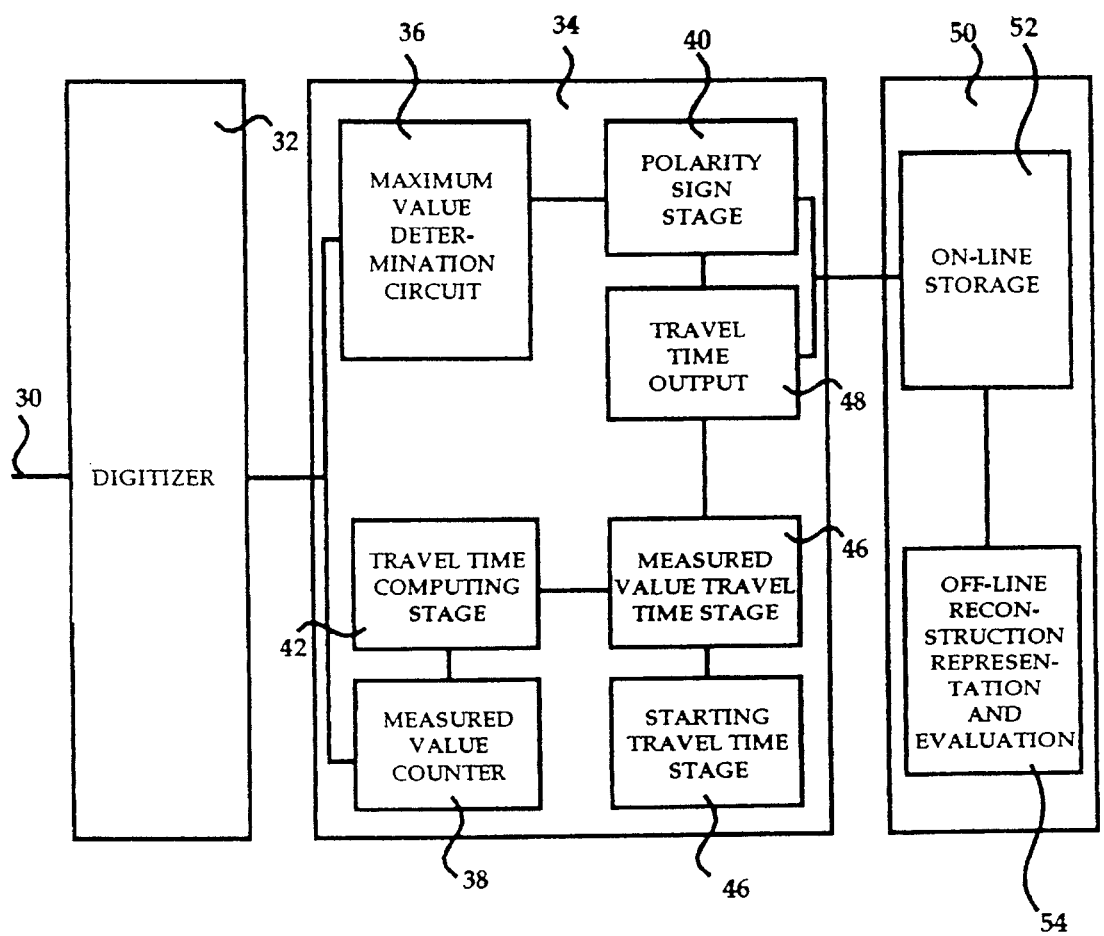

A connection diagram of the equipment used can be seen in FIG. 7. An analogue probe signal, according to the representation in FIG. 1, is present at an input 30 of a HF digitizer 32 and is digitized at a frequency of 300 MHz. The result shown in FIG. 3 is present at the output of the digitizer 32. In a downstream processing stage 34 the digitized values are fed on the one hand to a maximum value determination circuit 36 and on the other hand to a measured value counter 38. The maximum value determination circuit 36 determines a maximum value per half-wave and outputs this together with the corresponding polarity sign via a circuit 40. A travel time computing stage 42 is installed downstream of the measured value counter 38, which in turn is connected at its output to a measured value travel time stage 44. This latter stage receives the starting travel time in millimeters from a stage 46 and outputs the travel time value corresponding to the maximum value through a stage 48 "travel time output".

In this way the signals are available at the output of the processing stage 34 as can be seen from FIG. 4.

An on-line storage 52 for the reduced data is located in a downstream computing stage 50. It is connected with a stage 54 for off-line reconstruction, representation and evaluation. The reconstruction in this stage is effected corresponding to the algorithm stated above.

Figure 8:
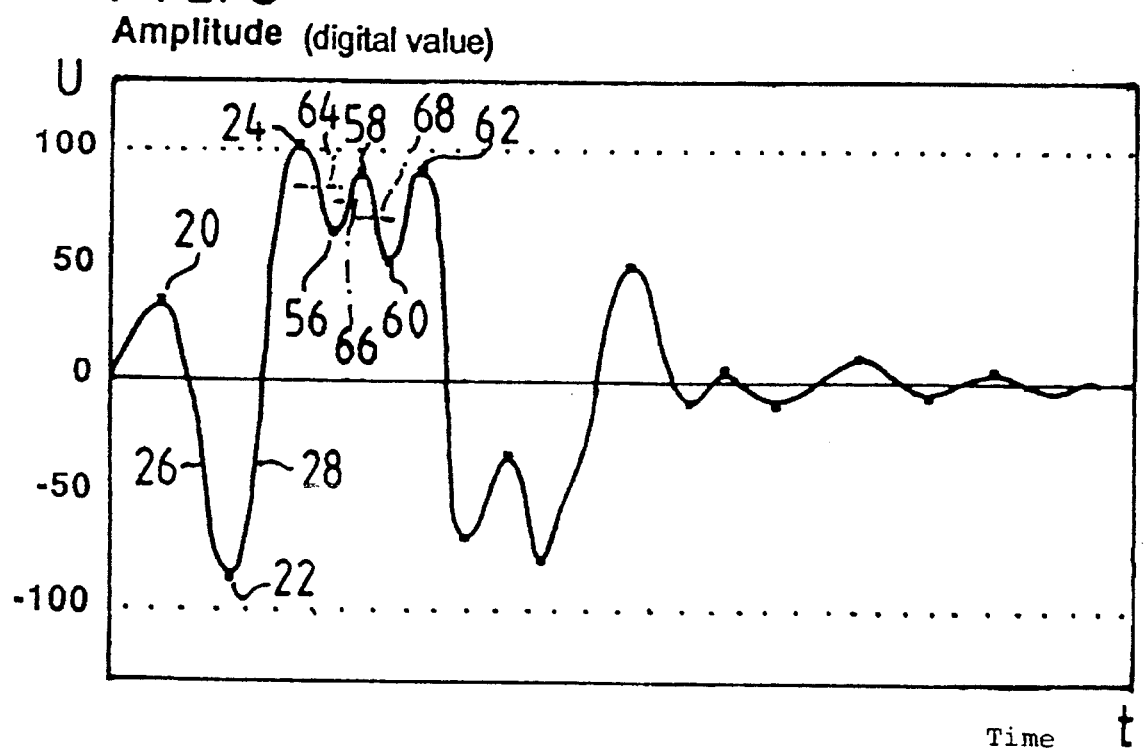

The signal waveform according to FIG. 8 differs from the signal waveforms seem until now according to FIGS. 1 to 6 in that several maximum amplitudes are passed through, namely true maximum values and intermediate relative minimum and maximum values, both in the positive and in the negative amplitude ranges, without in the meantime the signal waveform reaching the zero amplitude or even changing the polarity sign.

As FIG. 8 shows, the signal initially passes—as previously—through the node of interpolation 20 in the positive amplitude range and subsequently through the node of interpolation 22 in the negative amplitude range, and then again the node of interpolation 24 in the positive amplitude range. Until now there is no difference to the signal waveform discussed so far on the basis of FIGS. 1 to 6. After the node of interpolation 24 the signal now does not pass through the zero line, but reaches a (relative) minimum at node of interpolation 56, a new maximum at node of interpolation 58, a minimum at node of interpolation 60 and a maximum at node of interpolation 62, and with an amplitude change subsequently passes through two negative maximum amplitudes with an intermediate relative maximum amplitude.

This signal waveform is digitized and processed in the same way as discussed above, but a reference line is inserted as a zero reference, also known as a virtual zero line. Refer to the lines 64, 66 and 68, which have been added to illustrate this.

Therefore a maximum amplitude is to be understood as an area in the course of the signal curve, where an extreme value or extremum is present, where the slope therefore has the value zero, independent of the value of the second derivative, which may be positive or negative. It is inevitable that the value of the second derivative constantly changes its sign with maximum amplitudes in a time sequence. It is for example negative for the node of interpolation 24, positive for the node of interpolation 56, negative again for the node of interpolation 58, positive for the node of interpolation 60, etc. The invention makes it possible to reconstruct the waveform of the curve between such nodes of interpolation, regardless of whether a zero-crossing occurs between the successive nodes of interpolation. The virtual zero lines 64–68 are shown in such a way that they are essentially in the vicinity of the places where the second derivative of the signal has the value zero, i.e. where reversal points are present. Therefore, the virtual zero line 64 is drawn through the reversal point in the course of the curve between the nodes of interpolation 24 and 56. The same is true for the virtual zero line 66, which crosses the reversal point in the course of the curve between the nodes of interpolation 56 nd 58. It is assumed in a first approximation that the virtual zero line 64 is located in the middle between the two amplitude values of the nodes of interpolation 24 and 56, in other words equidistant from both. This is used in the practical implementation.

The method for the reconstruction corresponding to FIG. 6 is as described above and using the above-mentioned formula.

What is claimed is:

1. A method of processing an ultrasonic signal originating from a probe, having a probe frequency, the method comprising the following steps:

(a) digitizing the ultrasonic signal at a sample frequency, which is a multiple of the probe frequency;

(b) determining maximum amplitudes of the digitized ultrasonic signal, whereby maximum amplitudes are present where the slope of digitized ultrasonic signal has the value zero, and determining a time value and a polarity sign corresponding to each maximum amplitude;

(c) storing in a memory the maximum amplitude, the time value and the polarity sign corresponding to each of the maximum amplitudes of the digitized ultrasonic signal; and (d) reconstructing the ultrasonic signal by plotting the stored maximum amplitude, the stored time value and the stored polarity sign corresponding to the maximum amplitudes of the digitized ultrasonic signal and connecting any two neighboring maximum amplitudes with a 180 degree cosine curve having a slope of zero at each of the two neighboring maximum amplitudes.

2. The method of claim 1, wherein the digitizing of the ultrasonic signal occurs at a frequency of at least ten times the probe frequency.

3. The method of claim 2 wherein the step of digitizing the ultrasonic signal is performed by a high-frequency digitizer.

4. The method claim of claim 2 wherein the step of determining a maximum amplitude for the ultrasonic signal and a maximum value and a polarity sign corresponding thereto is performed by a maximum value determination circuit.

5. The method of claim 4 wherein the step of determining a maximum amplitude for the ultrasonic signal and a time value corresponding thereto is performed by a measured value counter.

6. The method of claim 5 wherein the step of digitizing the ultrasonic signal is performed by a high-frequency digitizer having an input and an output and wherein the digitizer input is connected to the probe and the digitizer output is connected to both the measured value counter and the maximum value determination circuit.

7. An apparatus for processing an ultrasonic signal comprising:

(a) a probe having a probe frequency, said probe used for measuring the ultrasonic signal;

(b) a digitizer which digitizes the ultrasonic signal from the probe at a sample frequency which is a multiple of the probe frequency;

(c) a maximum value determination circuit connected to the digitizer which determines maximum amplitudes of the digitized ultrasonic signal, whereby maximum amplitudes are present where the slope of the digitized ultrasonic has the value zero, and determining a corresponding polarity sign thereto;

(d) a measured value counter also connected to the digitizer for determining a time value corresponding to the maximum amplitudes of the digitized ultrasonic signal;

(e) a memory for storage of the maximum amplitude, the polarity sign and the time value corresponding to the maximum amplitude of the digitized ultrasonic signal; and (f) means for reconstructing the ultrasonic signal by plotting the stored maximum amplitude, the stored time value and the stored polarity sign corresponding to the maximum amplitudes of the digitized ultrasonic signal and connecting any two neighboring maximum amplitudes with a 180 degree cosine curve having a slope of zero at each of the two neighboring maximum amplitudes.

8. The apparatus of claim 7, wherein the probe has a probe frequency and the digitizer operates at a frequency of at least ten times the probe frequency.

9. An apparatus for processing ultrasonic signals originating from a probe, having a probe frequency, comprising:

(a) means for converting an analog ultrasonic signal to a digital ultrasonic signal;

(b) means for determining maximum amplitudes of the digitized ultrasonic signal, whereby maximum amplitudes are present where the slope of digitized ultrasonic signal has the value zero, and means for determining a time value and polarity sign corresponding to each maximum amplitude;

(c) a memory;

(d) means for storing in the memory the maximum amplitudes, the polarity sign and the time value corresponding to each of the maximum amplitudes; and (e) means for reconstructing the ultrasonic signal from the stored data by plotting the stored maximum amplitudes, the stored time value and the stored polarity sign corresponding to the maximum amplitudes of the digitized ultrasonic signal and connecting any two neighboring maximum amplitudes with a 180 degree cosine curve having a slope of zero at each of the two neighboring maximum amplitudes.

* * * * *